US006241721B1

(12) United States Patent
Cozean et al.

(10) Patent No.: US 6,241,721 B1
(45) Date of Patent: Jun. 5, 2001

(54) LASER SURGICAL PROCEDURES FOR TREATMENT OF GLAUCOMA

(76) Inventors: Colette Cozean, 21581 Midcrest, El Toro, CA (US) 92630; Michael Colvard, 1280 Piedra Morade, Pacific Palisades, CA (US) 90272; Robert C. Allen, 849 Flordon Dr., Charlottesville, VA (US) 22901; Edwin U. Keates, 1316 Wrenfield Way, Villanova, PA (US) 19085

( * ) Notice: Subject to any disclaimer, the term of this patent is extended or adjusted under 35 U.S.C. 154(b) by 0 days.

(21) Appl. No.: 09/169,258

(22) Filed: Oct. 9, 1998

(51) Int. Cl.[7] ................................................. A61B 18/18
(52) U.S. Cl. .......................... 606/6; 606/4; 606/5; 606/15
(58) Field of Search ............................. 606/6, 5; 128/1, 128/898, 276; 623/6; 604/2–4

(56) References Cited

U.S. PATENT DOCUMENTS

| | | |
|---|---|---|
| 4,309,998 | 1/1982 | Aron nee Rosa et al. . |
| 4,328,803 * | 5/1982 | Pape ..................................... 128/276 |
| 4,660,546 * | 4/1987 | Herrick et al. ........................ 128/1 R |
| 5,090,425 * | 2/1992 | Stahl .................................... 128/898 |
| 5,190,057 * | 3/1993 | Sarfarazi .............................. 128/898 |
| 5,336,262 * | 8/1994 | Chu ......................................... 623/6 |
| 5,360,425 | 11/1994 | Cho . |
| 5,370,641 * | 12/1994 | O'Donnell, Jr. .......................... 606/4 |
| 5,549,598 * | 8/1996 | O'Donnell, Jr. .......................... 606/6 |
| 5,738,677 * | 4/1998 | Colvard et al. ........................... 606/4 |

OTHER PUBLICATIONS

Chi, T.S.K, et al., "Holmium Laser Sclerostomy Via Corneal Approach With Adjuvant Transconjunctival Mitomycin C in Rabbits", *Abstract Book From the Association for Research in Vision and Ophthalmology; Investigative Ophthalmology & Visual Science Annual Meeting*, vol. 35, No. 4, Mar. 15, 1994, pp 2067.

Ruderman, J.M, et al., "Internal Trabeculotomy", *Abstract Book From the Association for Research in Vision and Ophthalmology; Investigative Ophthalmology & Visual Science Annual Meeting*, vol. 25, No. 3, Mar. 15, 1984, pp 44.

Cotter, F., et al., "Erbium–YAG Laser Ablation of Human Trabecular Meshwork Following Stenting of Schlem's Canal: A Histopathologic Study", *Abstract Book from the Association for Research in Vision and Ophthalmology; Investigative Ophthalmology & Visual Science Annual Meeting*, vol. 36, No. 4, Mar. 15, 1995, pp s838.

Cotter, F., et al., "Erbium–YAG Laser Ablation of Human Trabecular Meshwork with a Stent in Schlem's Canal: A Histopathologic Study", *Abstract Book from the 15th Annual Meeting of the American Society for Lasers in Surgery and Medicine*, San Diego, CA, Apr. 2–4, 1995, pp 30, published Mar. 1995.

Krasnov, M.M., "Q–Switched Laser Goniopuncture", *Arch Ophthalmol*, vol. 92, Jul. 1974, pp 37–41.

Krasnov, M.M., Q–Switched ("Cool") Lasers in Ophthalmology, pp 29–44.

Krasnov, M.M., "Laser–phakopuncture in the treatment of soft cataracts", *British Journal of Ophthalmology*, vol. 59, 1975, pp 96–98.

(List continued on next page.)

Primary Examiner—Linda C. M. Dvorak
(74) Attorney, Agent, or Firm—Knobbe, Martens, Olson & Bear, LLP

(57) ABSTRACT

A laser and a laser probe are used in conjunction with a suture to remove a blockage in Schlemm's canal. The suture is advanced into Schlemm's canal until the suture comes into contact with tissue blocking the canal. The laser probe follows the path of suture until the laser probe is proximal to tissue blocking the canal. The laser is activated to apply pulsed laser energy to the tissue blocking the canal, thereby ablating the occluding tissue to reopen Schlemm's canal.

3 Claims, 5 Drawing Sheets

OTHER PUBLICATIONS

Krasnov, M.M., "Q–Switched Laser Iridectomy and Q–Switched Laser Goniopuncture", Adv. Ophthal., vol. 34, 1977, pp 192–196.

Akopyan, Y.S., et al., "New Clinical Prospects for Applying Lasers with Q–Switching in Ophthalmology", vol. 46 No. 10, 1982, pp. 2000–2004.

Wheeler, C.B., "Laser Iridectomy", Phys. Med. Biol., vol. 22, No. 6, 1977, pp 1115–1135.

Kennedy, S.H., "Laser Filtering: An Outpatient Procedure", Ophthalmology, vol. 16, No. 1, Jan. 1, 1991, pp 1, 27, 28.

Fink, A.J., et al., "Management of Large Filtering Blebs With the Argon Laser", American Journal of Ophthalmology, vol. 101, Jun. 1986, pp 695–699.

L'Esperance, Jr., F.A., Ophthalmic Lasers: Photocoagulation, Photoradiation, and Surgery, 1983, 2nd edition, pp 529–538, 554.

Taboada, J., et al., "An Extreme Sensitivity in the Corneal Epithelium to Far UV ArF Excimer Laser Pulses", Aerospace Medical Association 1981 Meeting, San Antonio, TX, pp 98–99.

Berlin, M.S., et al., "Goniophotoablation: Excimer laser glaucoma filtering surgery", Laser and Light in Ophthalmology, vol. 2, No. 2, 1988, pp 17–24.

Berlin, M.S., "Excimer Laser Applications in Glaucoma Surgery", Ophthalmology Clinics of North America, vol. 1 No. 2, Dec. 1988, pp 1–9.

* cited by examiner

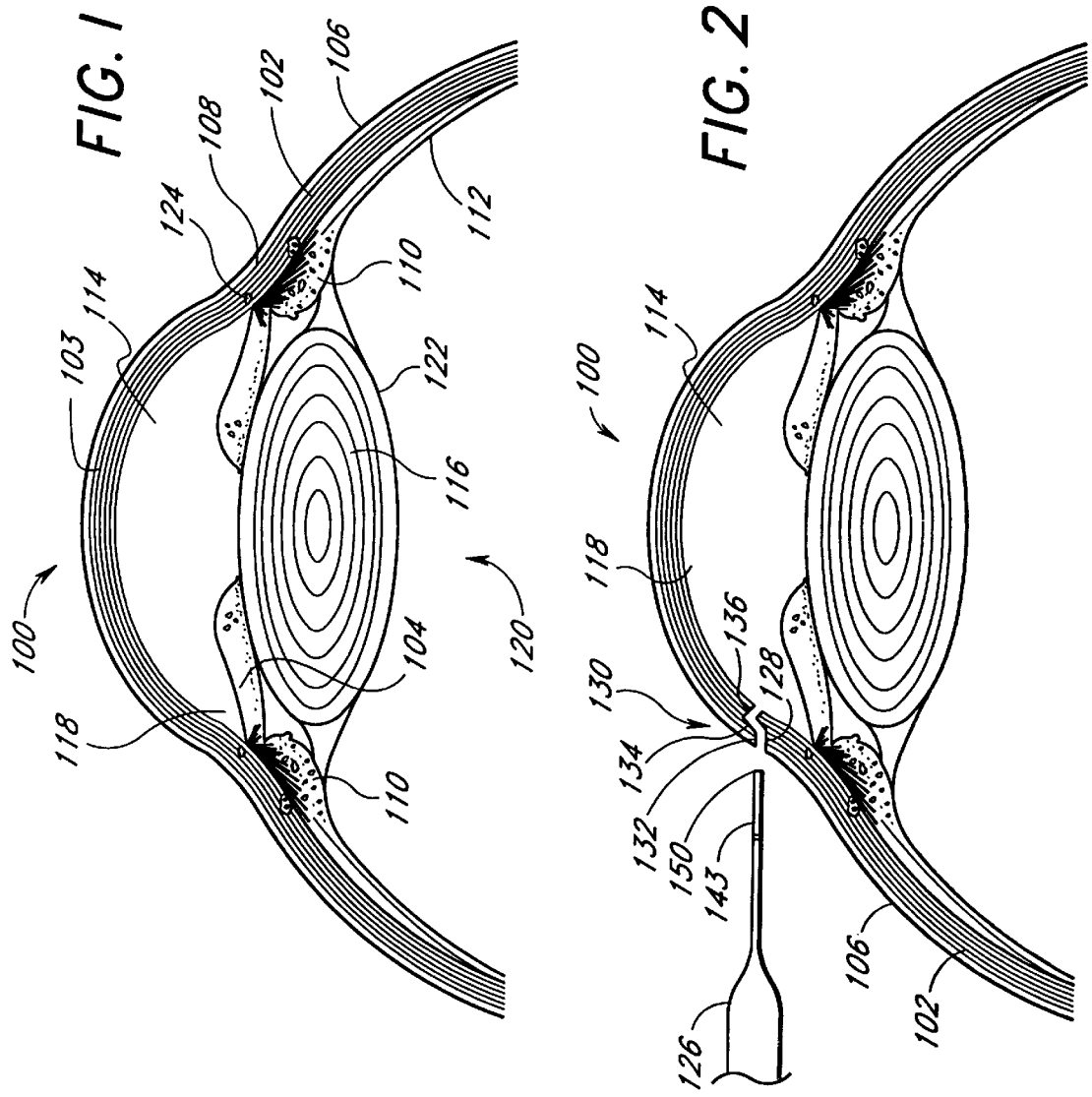

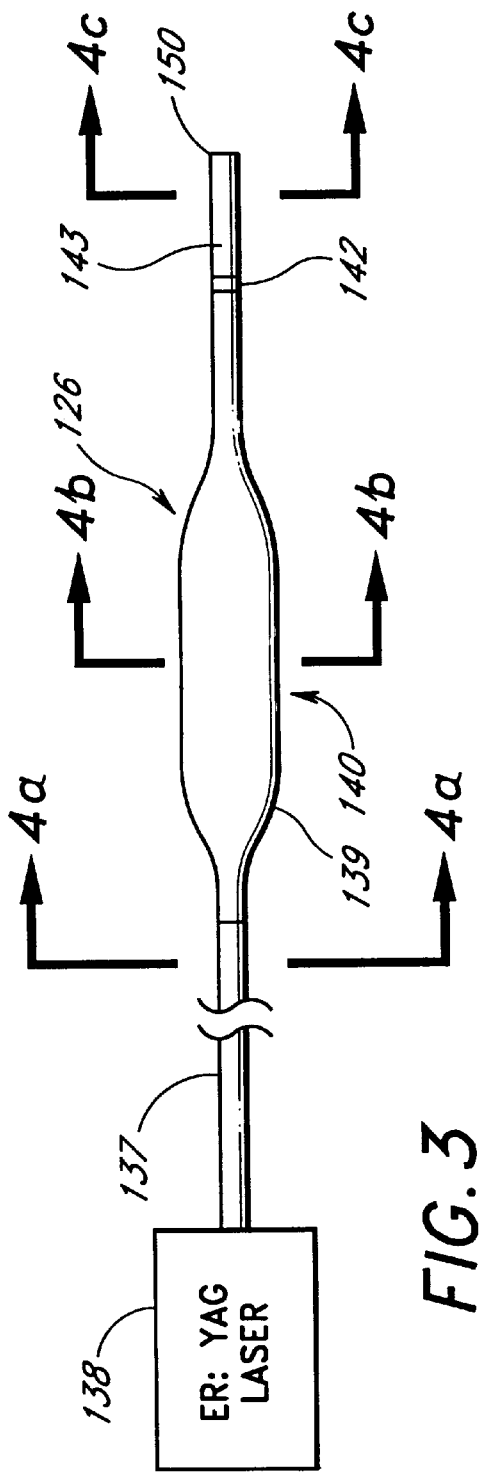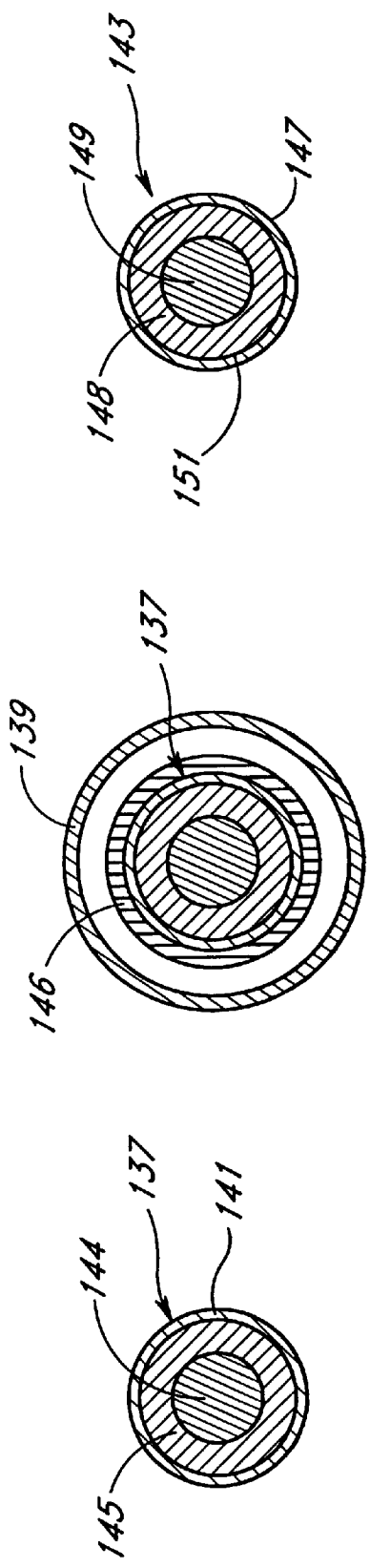

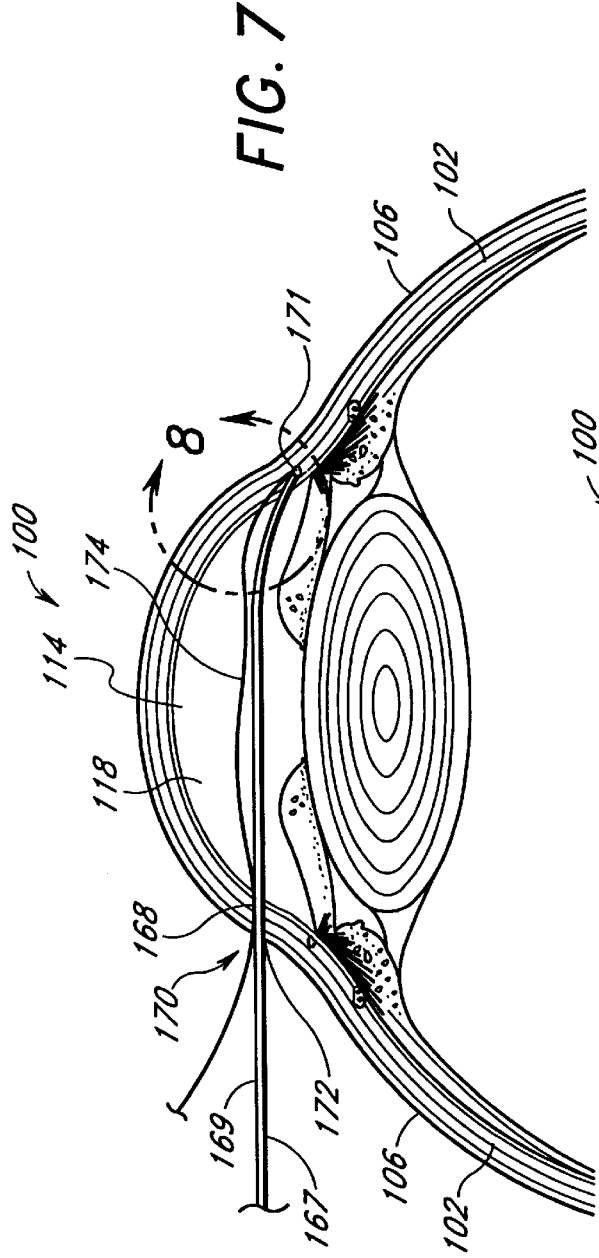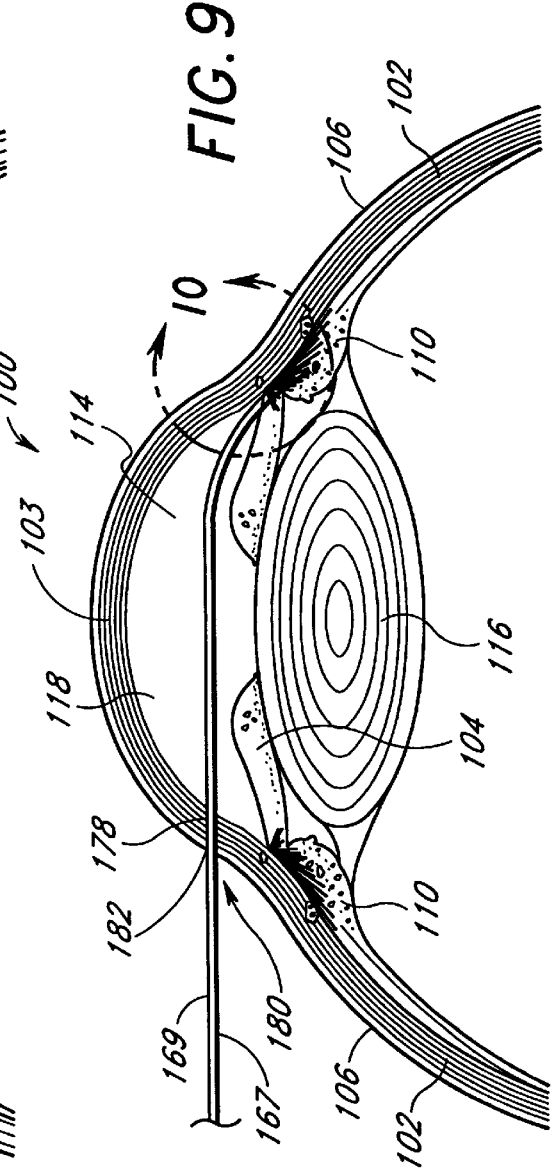

LASER SURGICAL PROCEDURES FOR TREATMENT OF GLAUCOMA

BACKGROUND OF THE INVENTION

The present invention relates generally to the field of laser surgery. More specifically, the present invention relates to a laser surgical procedure for treating glaucoma.

Glaucoma affects more than two million Americans and is the leading preventable cause of blindness in the United States. Glaucoma results from the body's inability to drain the clear, transparent liquid called the "aqueous humor", which flows through the inner eye continuously. Most commonly, the aqueous fluid drains from the anterior chamber to the sclera, through a variety of drainage channels or canals, such as the trabecular meshwork, the ciliary body, and through a natural channel in the eye called Schlemm's canal. These channels can become smaller with age, as they are clogged by deposits which build up slowly over time. In other cases, the channels are misformed at birth, and optimal drainage cannot be achieved without surgical intervention.

Without proper drainage of the aqueous humor from the anterior chamber, an abnormally high fluid pressure results within the eye which is referred to as glaucoma. As pressure builds up, the pressure can "pinch" both the optic nerve and the blood vessels which nourish the retina. The result is usually a slow loss of peripheral vision, and eventually blindness.

To treat glaucoma, it is conventional to form a channel in the sclera of the eye to drain aqueous fluid from the anterior chamber of the eye, thereby reducing the fluid pressure. The exit opening of the channel is covered by conjunctival tissue, which provides a filtering bleb. Typically, the channel in the sclera is made by a knife or other mechanical devices. These mechanical devices cause great trauma to the scleral tissue. Such trauma results in the formation of scar tissue which eventually obstructs the channel. Once the passageway is occluded, the aqueous humor will begin to build up in the anterior chamber again, which will result in the return of excess intraocular pressure and the failure of the procedure.

While it is possible that formation of a larger opening in the sclera would take longer to fill with scar tissue, if the hole is too large, an excess of aqueous humor will drain from the anterior chamber and will result in hypotony (i.e., excessively low intraocular pressure). Accordingly, when performing a standard glaucoma filtering procedure, it is desirable to ensure that the scleral opening is of sufficient size to allow for normalization of intraocular pressure, but not large enough to produce hypotony. If the opening is too small, the opening will close due to the build-up of scar tissue, and the procedure fails. Variables, including the degree of operative trauma caused by the mechanical procedure and the individual patient's response to this trauma, make it difficult to reliably predict the length of time a channel formed by a mechanical device will remain open. Typically, such channels remain open for at least one year. Since glaucoma tends to affect the elderly, it is not desirable to have to reschedule surgery on the eye on a yearly basis.

Recently, lasers, such as Nd:YAG and thalmium:YAG lasers, have been used as an alternative to mechanical devices to form the channels in the sclera tissue. These lasers, while providing less mechanical trauma to the sclera tissue than the mechanical procedures, still produce a high amount of heat and cause thermal trauma to the sclera. Since any type of trauma triggers the body's natural healing response, channels formed by Nd:YAG or thalmium:YAG lasers will eventually begin to form scar tissue that occlude the channel. Channels in the sclera formed by Nd:YAG or thalmium:YAG lasers remain open for 4–5 years at best.

Another common glaucoma treatment procedure involves forming a channel in the sclera to enable drainage of the aqueous humor using either a laser or a mechanical device and placing a stent in the channel in an attempt to keep the channel from narrowing. The stent may be effective to inhibit closure; however, the body may detect the stent as a foreign object and may start to form scar tissue at the stent site. Eventually the scar tissue can grow over the opening on either side of the stent and prevent drainage of the aqueous humor through the channel. Once the channel is closed, the stent must be removed and replaced, which involves additional surgical procedures.

SUMMARY OF THE INVENTION

One aspect of the present invention provides a method of treating glaucoma by performing an ab-extemo sclerotomy in an eye. The method comprises forming a passageway in the eye that is comprised of a plurality of interconnected segments. The segments are oriented so that the passageway follows a crooked, non-linear path through scleral tissue and terminates at the anterior chamber. The segments are sized to drain fluid from the anterior chamber so as to reduce intraocular pressure. In the preferred method, a first passageway segment is formed that extends from an exterior surface of the eye to the sclera of the eye. A second passageway segment is formed that extends from the first segment into the sclera at a substantial angle relative to the first passageway segment. The second segment preferably terminates within the sclera. A third passageway segment is formed that extends from the second segment through the sclera at a substantial angle relative to the second passageway segment. Preferably, the segments in the sclera follow respective paths that are inclined at a substantial angle relative to a line that is normal to the surface of the eye and passes through at least a portion of the passageway. The passageway segments are formed using laser energy from a laser probe which emits pulses of laser energy in a direction along its longitudinal axis. A V-shaped cut is made in the conjunctival tissue of the eye to permit entry of the probe into the eye. Preferably, the cut is a self-sealing cut and is located at the limbus. The first passageway segment is formed by placing the probe tip proximate to the tissue of the eye and advancing the probe as the laser is activated. The second segment is formed by positioning the probe tip within the first segment and applying a lateral force to the probe so as to align the longitudinal axis of the probe with the direction of the second passageway segment. With the probe tip positioned proximal to the targeted sclera tissue, the probe is advanced along the direction of the desired second segment as the laser is activated. The third segment is formed by positioning the probe tip within the first and second segments and applying a lateral force to the probe so as to align the longitudinal axis with the direction of the third passageway segment. With the probe positioned proximal to the targeted sclera tissue, the probe is advanced along the direction of the desired third segment as the laser is activated. In this manner, a nonlinear passageway is formed from three linear segments, with the first segment terminating at an end of the second segment and the second segment terminating at an end of the third segment. The passageway segments are sized so that each of the segments has substantially the same cross section. The cross section is selected so that (a) the second and third segments remain open for drainage of fluid after the probe is withdrawn, and (b) the first segment substantially self-seals when the probe is withdrawn to prevent substantial leakage of the fluid from the eye.

In another aspect of the present invention, an apparatus for performing an abextemo sclerotomy comprises single laser probe to form a passageway extending from an exterior of the eye through the sclera of the eye by emitting pulses of laser energy in a direction substantially along a longitudinal axis of the probe and advancing the probe through the passageway as it is formed. The probe is cross-sectionally sized so that the portion of the passageway extending through the sclera is greater than 350 microns in diameter when the probe is withdrawn. In addition, the probe is cross-sectionally sized so that a portion of the passageway adjacent the exterior of the eye substantially self-seals when the probe is withdrawn so as to prevent substantial leakage of fluid from the eye. In a preferred embodiment, the laser probe emits pulses of laser energy having an energy of about 10 to 15 mJ/pulse.

In another aspect of the present invention, the method of treating glaucoma comprises forming a first passageway segment that extends from an exterior surface of the eye to the sclera of the eye; and forming a second passageway segment that extends through the sclera along a crooked path.

In another aspect of the present invention, the method of treating glaucoma comprises a method of opening natural drainage structures of the eye which have become at least partially blocked using a laser and fiber delivery system. The method comprises transocularly advancing an optical fiber through the eye and positioning the fiber proximal to the occluded natural opening. The laser is activated to apply pulsed laser energy to the occlusion, thereby ablating the occluding tissue to reopen the blocked natural opening of the eye. Preferably, the laser is an Er:YAG laser which is pulsed at a pulse rate of about 5 to 10 Hz, a pulse duration of about 250 $\mu$s to 300 $\mu$s, and produces energy of about 10 to 15 mJ per pulse. In one embodiment, the natural drainage structure that is at least partially blocked is in the ciliary process. In another embodiment, the natural drainage structure is in the trabecular meshwork. In still another embodiment, the natural drainage structure is Schlemm's canal.

In another aspect of the present invention, the method of treating glaucoma comprises a method of removing a blockage in Schlemm's canal using a laser and a laser probe. The method comprises advancing a suture into Schlemm's canal until the suture comes into contact with tissue blocking the canal. A laser probe is inserted into the eye and follows the path of the suture until the laser probe comes into contact with the tissue blocking the canal. The laser is activated to apply pulsed laser energy to the tissue blocking the canal thereby ablating the occluding tissue to reopen Schlemm's canal. In one embodiment, the laser is an Er:YAG laser which is pulsed at a pulse rate of about 5 to 10 Hz, a pulse duration of about 250 $\mu$s to 300 $\mu$s, and produces energy of about 10 to 15 mJ per pulse.

In a further aspect of the present invention, a laser probe comprising a probe tip having a longitudinal axis is configured for use in the treatment of glaucoma. The probe tip is configured for insertion into conjunctiva tissue of an eye and comprises an optical fiber having a core which emits light in a direction along the longitudinal axis. The optical fiber core is surrounded by a stiffening layer which provides sufficient rigidity to the tip to allow the fiber tip to manipulate tissue such that a crooked pathway is formed through the sclera. The probe tip also has a sufficiently small diameter to cause the conjunctiva tissue to substantially self-seal when the probe is withdrawn. The diameter of the probe tip is greater than 350 microns to yield a passageway in the interior structures of the eye which is sufficiently large for reliable drainage of fluid, but is preferably less than 600 microns. In a preferred embodiment, the diameter of the probe tip is about 400–450 microns. In a preferred embodiment, the stiffening layer comprises a buffer layer.

BRIEF DESCRIPTION OF THE DRAWINGS

FIG. 1 is a cross-sectional view of a human eye.

FIG. 2 is a cross-sectional view of a human eye undergoing an ab-extemo sclerotomy procedure.

FIG. 3 is a schematic view of a laser and optical delivery probe used in the procedure of FIG. 2.

FIG. 4a is a cross-sectional view of the first optical fiber of FIG. 3.

FIG. 4b is a cross-sectional view of the probe tip of the laser probe of FIG. 3.

FIG. 4c is a cross-sectional view taken along line 4c—4c in FIG. 3.

FIG. 7 is a cross-sectional view of a human eye undergoing a procedure to reopen Schlemm's canal which has become partially blocked.

FIG. 9 is a cross-sectional view of a human eye undergoing a procedure to reopen the openings in a ciliary body which have become blocked.

DETAILED DESCRIPTION OF THE INVENTION

Figure 5:
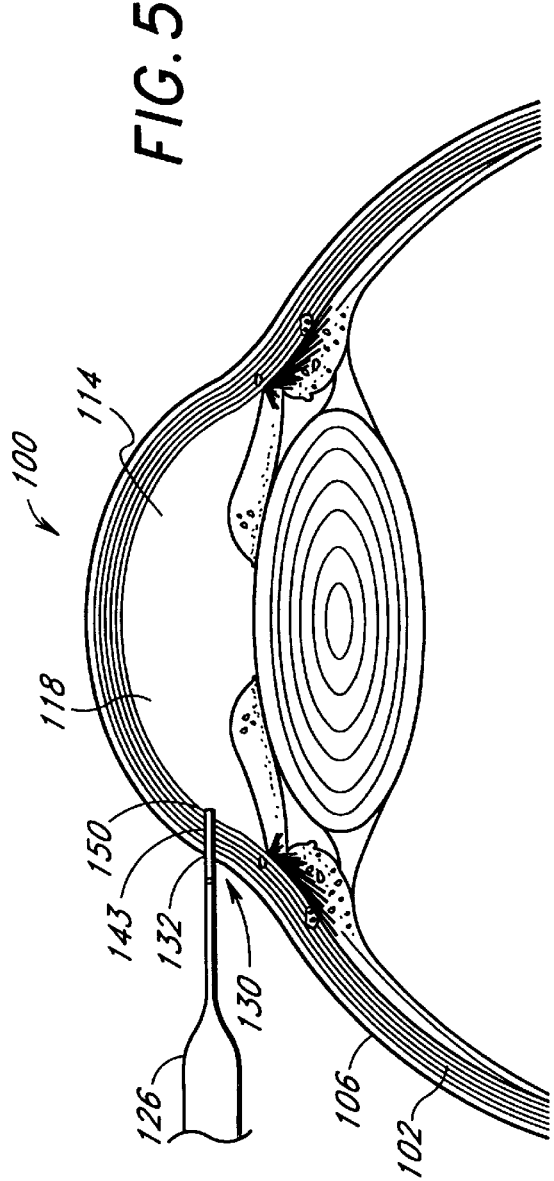
FIG. 5 is a cross-sectional view of a human eye undergoing an alternate abexterno sclerotomy procedure.

Referring to FIG. 1, relevant structures of the eye will be briefly described, so as to provide background for the anatomical terms used herein. Certain anatomical details, well known to those skilled in the art, have been omitted for clarity and convenience.

As shown in FIG. 1, the cornea 103 is a thin, transparent membrane which covers the iris 104. The cornea 103 merges into the sclera 102 at a juncture referred to as the limbus 108. A layer of tissue called bulba conjunctiva 106 covers the exterior of the sclera 102. The bulba conjunctiva 106 is thinnest anteriorly at the limbus 108 where it becomes a thin epithelial layer which continues over the cornea 103 to the corneal epithelium. As the bulba conjunctiva 106 extends posteriorly, it becomes more substantial with greater amounts of fibrous tissue. The bulba conjunctiva 106 descends over Tenon's capsule approximately 3 millimeters from the limbus 108. Tenon's capsule is a thicker and more substantial encapsulatory tissue which covers the remaining portion of the eyeball. The subconjunctival and sub-Tenon's capsule space become one when these two tissues meet, approximately 3 millimeters from the limbus 108. The ciliary body or ciliary process 110 is a meshwork of tissues having openings thereon. It begins at the limbus 108 and extends along the interior of the sclera 102. The choroid 112 is the vascular membrane which extends along the retina (not shown) back towards the optic nerve (not shown). The anterior chamber 114 of the eye is the space between the cornea 103 and a crystalline lens 116 of the eye. The crystalline lens 116 of the eye is situated between the iris 104 and the vitreous body 120 and is enclosed in a transparent membrane called a lens capsule 122. The anterior chamber 114 is filled with aqueous humor 118, a clear, transparent liquid which flows through the inner eye continuously. The trabecular meshwork 121 removes excess aqueous humor 118 from the anterior chamber 114 through Schlemm's canal 124 through veins which merge with blood-carrying veins to take the aqueous humor 118 away from the eye. The ciliary body 110 also aids in the drainage of fluid from the anterior chamber 114 of the eye.

The laser procedures of the present invention are performed on the eye 100 to relieve glaucoma. As is well known to those of skill in the art, glaucoma is a condition which involves the build-up of excess intraocular pressure within the eye 100 due to improper drainage of the aqueous humor 118 from the anterior chamber 114. Commonly, the natural drainage structures of the eye 100, such as the trabecular meshwork 121, Schlemm's canal 124, and the ciliary body 110, become at least partially occluded with age as they are clogged by deposits which build up slowly over time. Alternatively, these natural drainage structures may have been deformed at birth. The pressure in the eye 100 may be relieved by reopening the natural drainage structures of the eye or by forming new channels or passageways within the eye 100 to drain the fluid from the anterior chamber 114. These passageways may be formed by the surgeon starting from the interior of the eye 100, referred to as an ab-interno procedure, or from the exterior of the eye 100, referred to as an ab-externo procedure.

As illustrated in FIG. 2, in an ab-externo sclerotomy procedure, a single laser probe 126, shown in FIG. 3, is used to form a passageway 128 extending from an exterior 130 of the eye 100 through the sclera 102 of the eye 100. The probe 126 is connected to receive light from a laser 138.

Preferably, the laser 138 comprises an erbium doped laser which provides light having a wavelength of 2.94 microns in the mid-infrared portion of the optical spectrum. Use of an erbium doped laser, such as an Er:YAG laser 138, is advantageous because it requires less power to ablate the eye tissue than do the Nd:YAG and thalmium:YAG lasers of the prior art. Preferably, the Er:YAG laser 138 has a pulse repetition rate of 5 to 10 Hz, a pulse duration of 250 $\mu$s to 300 $\mu$s, and a pulse energy of 10 to 15 mJ per pulse. Since mid-infrared wavelengths, such as produced by the Er:YAG laser, are invisible to the naked eye, a visible beam, such as produced by a HeNe laser, is used to provide a target spot for the laser energy. Using an Er:YAG laser 138 at the above parameters limits the thermal damage of surrounding tissue to a depth of 5 to 50 microns. By reducing the depth of the thermal damage, the amount of scar tissue buildup caused by the laser is minimal. Thus, the likelihood that the passageway 128 will become blocked with scar tissue is reduced, and the likelihood that the procedure will need to be repeated is reduced.

The Er:YAG laser 138 is connected to supply light to a first optical fiber 137. The first optical fiber 137 is preferably a fluoride fiber. In an alternate embodiment, the fiber may be a sapphire fiber or other metal halide or oxide fibers. Referring to FIG. 4a, the first optical fiber 137 comprises a core 144 which guides light in a direction along the longitudinal axis, a cladding 145 which surrounds the core 144, and a buffer 141 which provides rigidity to the fiber. Preferably, the core 144 and cladding 145 are comprised of zirconium fluoride, and the buffer 141 is comprised of polyemide. Alternatively, the buffer 141 can be made from acrylate or peak.

The fiber 137 is connected to a handpiece or laser probe 126. In the preferred embodiment, the handpiece 126 comprises a main body 140 and a probe tip 143. The probe tip 143 is attached to the main body 140 by a brass ferule 142 which enables the probe tip 143 to be screwed onto the end of the main body 140 of the handpiece 126. In an alternate embodiment, the probe tip 143 is made longer and is attached to the fiber 137 within the center of the main body 140 of the handpiece.

The main body 140 of the handpiece 126 comprises a plastic housing 139 within which the distal end of the optical fiber 137 is contained. The plastic housing 139 is provided to enable easy manipulation of the handpiece by the user. The optical fiber 137 is surrounded by a thin stainless steel tube or sheath 146 once it enters the handpiece 126 to provide some rigidity to the fiber within the handpiece 126. The optical fiber 137 is rigidly attached to the stainless steel tube 146 which is in turn rigidly attached to the plastic housing 139 of the handpiece 126 by conventional means to prevent substantial relative movement between the fiber 137 and the handpiece 126. In the preferred embodiment the stainless steel tubing 146 extends from the main body 140 of the handpiece 126 to the brass ferule 142 where the probe tip 143 is attached.

Referring to FIG. 4b, the probe tip 143 comprises a second optical fiber 147. In the preferred embodiment, the second optical fiber 147 is a sapphire or quartz fiber. Alternatively, the second optical fiber 147 may be another type of fluorophosphate fiber which is bio-compatible. In one embodiment, the first optical fiber 137 and the second optical fiber 137 are the same fiber, thus the brass ferule 142 is not needed. In the preferred embodiment, the second optical fiber 147 comprises a core 149 which guides light in a direction along the longitudinal axis, a cladding 148 which surrounds the core 149 and a buffer 151 which surrounds the core 149. The buffer 151 provides sufficient rigidity to the fiber to manipulate the tissue within the range of its elasticity when a lateral force is applied to the probe 126. Preferably, the core 148 and the cladding 149 are comprised of sapphire or quartz. The buffer 151 is made from polyemide. Other possible materials which the buffer 151 can be made from include acrylate and peak. A portion of the probe tip 143 is covered by a stainless steel sheath or tube 146 to provide additional rigidity to the second optical fiber 147. Preferably, the stainless steel tube 146 covers approximately 2–4 mm of the probe tip 143 extending from the brass ferule 142 where the probe tip 143 is attached towards the distal end 150 of the tip. The probe tip 143 is the portion of the probe 126 that is inserted into the eye. However, in the preferred embodiment, the portion of the probe tip 143 which contacts the interior layers of the eye does not include the stainless steel tube 146, and only the second optical fiber 147 is inserted into the eye. For use in ab-extemo sclerotomy procedures, the portion of the probe tip 143 which is inserted into the eye is preferably about 7 mm long. For use in the ab-intemo sclerotomy procedure described below, the portion of the probe tip 143 which is inserted into the eye is preferably about 17 mm long.

Preferably, the probe tip 143 is sized to be sufficiently small in diameter to enable the conjunctiva 106 to substantially self-seal when the probe 126 is withdrawn. In a preferred embodiment, the diameter of the probe tip 143 is greater than 350 microns to yield the passageway 128 in the interior structures of the eye 100, which is sufficiently large enough for reliable drainage of fluid. The diameter of the probe tip 143 is preferably less than 600 microns to enable the first passageway segment 132 through the conjunctiva 106 to self-seal. More preferably, the diameter of the probe tip 143 is about 400 to 450 microns. The diameter of the fiber core 149 of the probe tip 143 is preferably 200 to 500 microns and is uniform along its length. More preferably, the diameter of the fiber core 149 of the probe tip 143 is 400 microns. Preferably, the thickness of the cladding layer 148 is no more than 5 to 20 percent of the core diameter. In the preferred embodiment, the cladding layer 148 has a thickness of 20 to 40 microns. Preferably, the thickness of the buffer layer 151 is no more than 2 to 20 percent of the core diameter. In the preferred embodiment, the buffer layer 148 has a thickness of 8 to 80 microns.

The ab-externo sclerotomy procedure begins with the surgeon forming a V-shaped incision 132 in the conjunctiva 106 of the eye 100 to permit entry of the probe 126 into the eye 100. The incision 132 is made using a razor-sharp pointed blade. Preferably, the incision 132 is less than 1.5 millimeters in length and more preferably less than 1 millimeter in length. The incision 132 is located at the limbus in the conjunctiva 106. Since the conjunctiva 106 is a gelatinous material, and provided the incision is not too large, such an incision 132 will be self-sealing, that is, the tissue of the conjunctiva 106 will grow back together without the need of stitches or other connective measures.

The laser 138 emits pulses of laser energy which propagate through the first optical fiber 137 and the second optical fiber 147 in a direction along the longitudinal axis of each of the fibers 137, 147, respectively. The probe tip 143 is inserted into the incision site 132, and the laser is activated to remove tissue and form the passageway 128 in the eye 100. The passageway 128 is comprised of a plurality of passageway segments 130. A first passageway segment 132 is formed in the conjunctiva 106 by positioning the fiber tip 143 with the incision proximate to targeted conjunctival tissue 106. The fiber tip 143 is advanced through the conjunctival tissue 106 as the laser is activated until the tip 143 reaches the sclera 102. A second segment 134 of the passageway 128 is formed that extends from the first passageway segment 132 into the sclera 102 at a substantial angle relative to the first passageway segment 132. With the probe tip 143 positioned in the first segment 132 and a distal end 150 of the probe tip 143 at the end of the segment 132, a lateral force is applied to the probe tip 143 to position the second fiber 147 of the probe tip 143 at the desired angle relative to the first passageway segment 132. Such force deforms the tissue sufficiently to align the longitudinal axis of the fiber 147 with the desired direction of the second passageway segment 134. The tip 143 is maintained in such alignment while the laser is activated to ablate tissue and form the passageway segment 134. The tip 143 is advanced as the laser is activated to complete the second passageway segment 134 through the sclera 102. A third segment 136 of the passageway is formed that extends from the second passageway segment 134 through the sclera 102 at a substantial angle relative to the second passageway segment 134. With the probe tip 143 in both the first and second passageway segments 132, 134 and the distal end 150 of the tip 143 at the end of the second segment 134, a lateral force is applied to the probe tip 143. The force distorts the tissue sufficiently so as to position and align the fiber 147 at the desired angle relative to the second passageway segment 134. While maintaining the alignment of the probe tip 143, the probe is advanced as the laser ablates tissue to form the third segment 136. The probe 126 is continuously advanced until the passageway 128 passes completely through the sclera 102 and opens into the anterior chamber 114 of the eye 100. Once the passageway 128 through the sclera 102 is complete, the probe 126 is withdrawn from the eye 100. After the probe 126 is withdrawn, the tissue returns to a "relaxed" state such that the portion of the passageway 128 that extends through the sclera 102 follows a crooked, nonlinear path comprised of three linear segments, each having substantially the same cross section. The first passageway segment 132 through the conjunctiva 106 preferably self-seals to form a "bleb," thereby preventing too much drainage of aqueous humor 118 from the anterior chamber 114 through the passageway 128. Preferably, the passageway 128 is cross-sectionally sized so that the portion of the passageway 128 extending through the sclera 102 is greater than 350 microns in diameter when the probe 126 is withdrawn.

In another ab-externo procedure, illustrated in FIG. 5, the single laser probe 126 as illustrated in FIGS. 3 and 4 is used to form a passageway 150 extending from an exterior 130 of the eye 100 through the sclera 102 of the eye 100 by emitting pulses of laser energy in a direction substantially along a longitudinal axis of the fiber and by advancing the probe tip 143 through the passageway 150 as it is formed. In an alternate embodiment, the laser probe or handpiece may be replaced with a bare optical fiber comprising a core, a cladding layer and a buffer layer of similar characteristics as the second optical fiber 147 which forms the probe tip 143. As in the ab-externo sclerotomy procedure described above, the procedure begins with the surgeon forming a V-shaped self-sealing incision 132 in the conjunctiva 106 of the eye at the limbus to permit entry of the probe into the eye 100 using a razor-sharp pointed blade. The passageway 150 extends from the exterior 130 of the eye 100 through the sclera 102 and terminates in the anterior chamber 114 of the eye 100. The probe tip 143 is advanced through the conjunctiva 106 as the laser is activated to emit pulses of laser energy along the longitudinal axis of the fiber 153 toward the targeted tissue. Once the probe tip 143 has passed through the conjunctiva 106, the laser probe 126 continues to be linearly advanced through the sclera 102 while the laser is activated to emit pulses of laser energy. The probe tip 143 is continuously linearly advanced through the sclera 102 while the laser is activated until the passageway 150 extends completely through the sclera 102 and opens into the anterior chamber 114 of the eye 100.

The probe tip 143 is cross-sectionally sized so that a portion of the passageway 150 which extends through the sclera 102 remains open for the drainage of fluid after the probe 125 is withdrawn. Preferably, the passageway 150 is cross-sectionally sized so that the portion of the passageway 150 extending through the sclera 102 is greater than 350 microns in diameter when the probe 125 is withdrawn. In addition, the passageway 150 is cross-sectionally sized so that a portion of the passageway 150 adjacent the exterior 130 of the eye 100 substantially self-seals when the probe 125 is withdrawn to prevent substantial leakage of the aqueous humor 118 from the eye 100.

Figure 6:
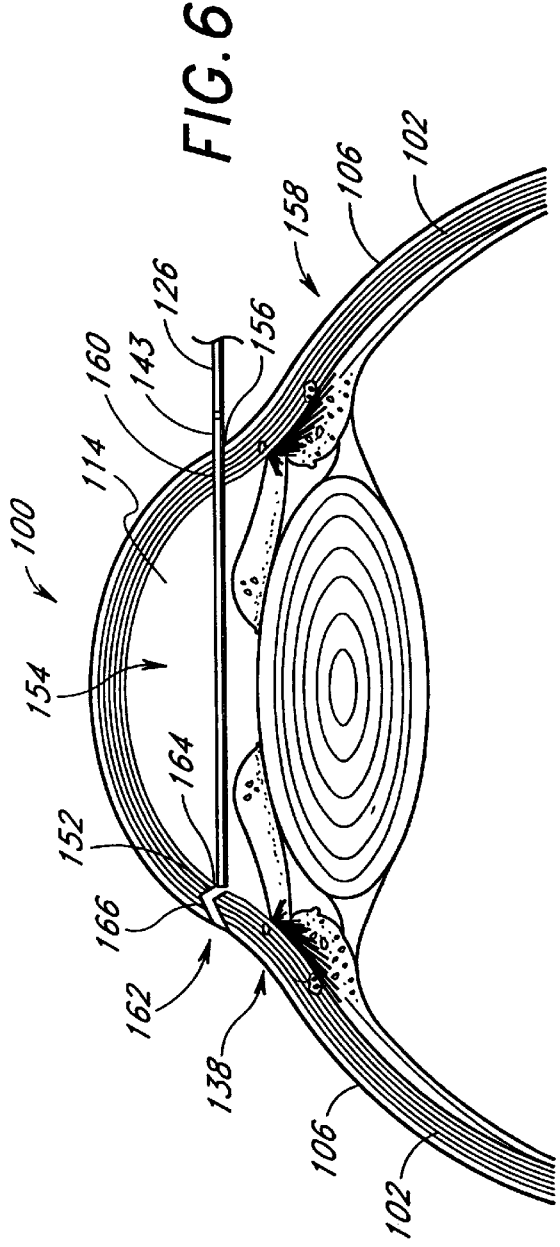
FIG. 6 is a cross-sectional view of a human eye undergoing an ab-interno sclerotomy procedure.

In an ab-interno procedure, illustrated in FIG. 6, the single laser probe 126 shown in FIGS. 3 and 4 is used with the probe tip 143 having an extended length to form a passageway 152 extending from an interior 154 of the eye 100 through the sclera 102 to the exterior 138 of the eye 100. The ab-interno sclerotomy procedure begins with the surgeon forming a self-sealing V-shaped incision 156 in the conjunctiva 106 at the limbus. The incision 156 is on the side 158 of the eye 100 opposite to the side 162 where the desired passageway 152 is to be formed. The purpose of the incision 156 is to permit entry of the probe 126 into the eye 100 as described in association with the ab-externo sclerotomy procedure above. With the laser probe tip 143 inserted into the incision 156, the laser probe tip 143 is advanced through the conjunctiva 106 as the laser 138 (FIG. 3) is activated. Once the laser probe tip 143 has passed through the conjunctiva 106, the laser probe tip 143 continues to be advanced through the sclera 102 while the laser 138 is activated to emit pulses of laser energy until a first channel 160 passes completely through the sclera 102 and opens into the anterior chamber 114 of the eye 100. As will be recognized by those of skill in the art, this first channel 160 may be formed by mechanical means rather than by the laser 138 and laser probe 126. For example, a scalpel may be used to cut a channel through the conjunctiva 106 and sclera 102. The laser probe tip 143 is transocularly advanced through the first channel 160, through the anterior chamber 114 of the eye 100, until the probe tip 143 is proximal to the sclera 102 on the opposite side 162 of the eye 100.

A first segment 164 of the passageway 152 is formed at a substantial angle relative to the channel 160 formed at the opposite side 158 of the eye 100. This is accomplished by positioning the laser probe tip 143 against the sclera 102 inside the eye and applying a lateral force to the laser probe 126. This force distorts the tissue sufficiently to position and align the probe 126 at a substantial angle relative to the first channel 160, thus aligning the longitudinal axis of the probe 126 with the desired direction of the first segment 164 of the passageway 152. With the probe 126 so aligned, the laser 138 is activated, and the probe tip 143 is advanced along a path corresponding to the first segment 164 as the laser pulses remove tissue to form the segment 164. Once the first passageway segment 164 has been formed, a second segment 166 of the passageway 152 is formed from the first passageway segment 164 through the sclera 102 at a substantial angle relative to the first passageway segment 164. This is accomplished by applying a lateral force to the probe 126 to position the probe 126 at the desired angle relative to the first passageway segment 164. The probe tip 143 is advanced along the path corresponding to the segment 166 as the laser 138 is activated until the second passageway segment 166 passes completely through the sclera 102. Once the passageway 152 is complete, the probe tip 143 is withdrawn from the passageway 152, through the anterior chamber 114, and through the channel 160. The tissue surrounding the passageway, being no longer distorted by the probe, elastically returns to its natural condition such that the portion of the passageway 152 that extends through the sclera 102 follows a crooked, nonlinear path. The channel 160 is sealed either by suturing or else it is left to self-seal. The passageway 152 remains open, and the aqueous humor 118 is able to drain from the anterior chamber 114 through the passageway 152 in the sclera 102 that has been created.

The segments of the passageway 152 are preferably sized so that each of the segments has substantially the same cross-section. The cross-section is selected so that the passageway 152 remains open for the drainage of fluid after the probe 126 is withdrawn. Preferably, the passageway 152 is cross-sectionally sized so that the portion of the passageway 152 extending through the sclera 102 is greater than 350 microns in diameter when the probe 126 is withdrawn.

Figure 8:
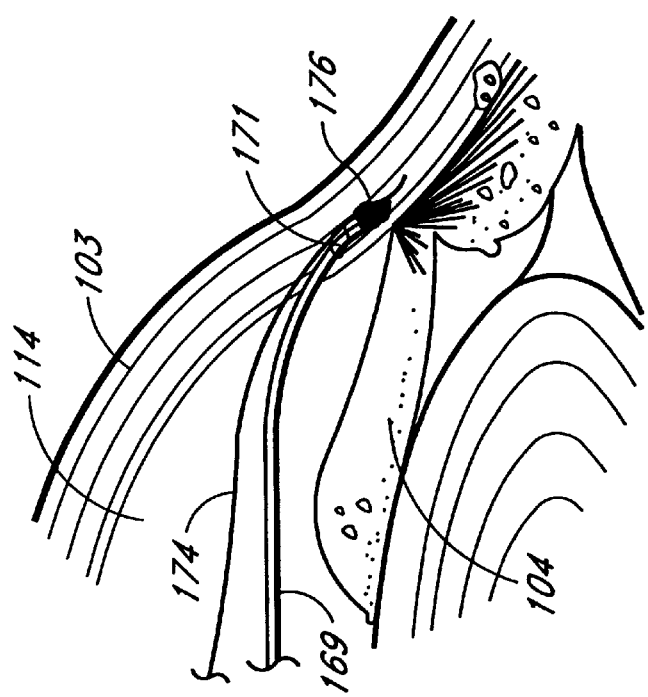
FIG. 8 is an enlarged view of the portion of a human eye indicated in FIG. 7 which is undergoing the procedure to reopen Schlemm's canal.

In yet another procedure, illustrated in FIGS. 7–8, a laser probe is used to open the natural drainage structures of the eye 100 that have at least become partially blocked. As described above, the aqueous fluid 118 drains from the anterior chamber 114 to the sclera 102, through a variety of drainage channels or canals, such as the trabecular meshwork 121, the ciliary body 110, and through a natural channel in the eye called Schlemm's canal 124. These channels can become smaller with age and may be clogged by deposits which build up slowly over time. In other cases, the channels are misformed at birth and optimal drainage cannot be achieved without surgical intervention.

In a first embodiment, the Er:YAG laser 138 (FIG. 3) is used to reopen a blocked Schlemm's canal 124. The laser 138 is coupled to a laser probe 167 comprising a flexible optical fiber 169 such as a sapphire fiber. In the preferred embodiment, the optical fiber 169 comprises a core which guides light in a direction along the longitudinal axis, a cladding which surrounds the core and a buffer which surrounds the core. The buffer provides sufficient rigidity to the fiber to manipulate the tissue within the range of its elasticity when a lateral force is applied to the fiber. Preferably, the core and the cladding are comprised of sapphire. The buffer is made from polyemide. Other possible materials which the buffer can be made from include acrylate and peak. Preferably, the fiber 169 has a core diameter of 200 to 600 microns. In the preferred embodiment, the cladding layer has a thickness of no more than 5 to 20 percent of the core diameter and the buffer layer has a thickness of no more than 2 to 20 percent of the core diameter. Alternatively, the flexible optical fiber 169 may be connected to the laser probe 126 of FIGS. 3 and 4 utilizing the probe tip 143 of the extended length for the ab-interno sclerotomy procedure. The fiber 169 delivers light pulses from the laser at a wavelength of 2.94 microns to form a first passageway 168 in the side 170 of the eye that is opposite from the side 170 containing the blocked Schlemm's canal 124. The surgeon forms a self-sealing V-shaped incision 172 in the conjunctival tissue 106 in the side 170 to permit entry of the fiber 169 into the anterior chamber of the eye 100, as described in association with the ab-interno sclerotomy procedure above. The fiber 169 is inserted into the incision site 172 and is advanced through the conjunctiva tissue 106 as the laser 138 (FIG. 3) is activated to emit pulses of laser energy along the longitudinal axis of the fiber toward the targeted tissue in the conjunctiva 106. Once the end 171 of the fiber 169 has passed through the conjunctiva 106, the laser probe continues to be advanced through the sclera 102 while the laser is activated to emit pulses of laser energy until the first channel extends completely through the sclera 102 and opens into the anterior chamber 114 of the eye 100. As will be recognized by those of skill in the art, this first channel may be formed by mechanical means rather than by the laser 138 and fiber 169. For example, a scalpel may be used to cut trough the conjunctiva 106 and sclera 102.

A suture 174 is placed through the first channel into the anterior chamber 114 and is then inserted into the partially blocked Schlemm's canal 124. The suture 174 is fed down the length of Schlemm's canal 124 until the blocked portion of the canal 124 is reached and then the suture 174 is pushed into the blocked canal 124. Preferably, the suture 174 is a made from nylon about 1 to 1.2 mm in diameter, and is sufficiently stiff to permit it to be advanced down Schlemm's canal 124 to the site of the blockage and into a small remnant of the original canal 124 where the blockage is located. The laser probe 126 is advanced through the first channel into the anterior chamber 114 of the eye 100 and into Schlemm's canal 124. The suture 174 acts as a mechanical guide for the fiber 169 which tends to follow the path of the suture 174 as it is forced into the canal 124. The fiber 169 is advanced until the end 171 of the fiber 169 is proximal to or is in contact with the blocking tissue 176, but no further down the canal 124 than the suture 174, and preferably not as far into the canal as the end of the suture. In this position, the longitudinal axes of the suture, the fiber, and Schlemm's canal are locally aligned so that pulses emitted from the end 171 of the fiber are precisely directed into the small remnant of the original canal and along the path of the original canal. The laser is activated for several pulses to ablate the blocking tissue 176. Such ablation removes a portion of the tissue 176 so as to permit the suture 174 to be advanced down the canal 124. The fiber 169 is advanced as well, and the laser 138 is again activated for several pulses until the tissue 176 is further ablated. The process of advancing the suture 174, advancing the fiber 169, and firing the laser 138 is repeated until the blocking tissue 176 is removed from the Schlemm's canal. With the blocking tissue 176 removed from the canal 124, the aqueous humor 118 from the anterior chamber 114 can once again flow from the anterior chamber 114 through Schlemm's canal 124 to maintain the desired pressure within the eye 100, thus relieving the glaucoma condition. Advantageously, the Er:YAG laser can be used at low power levels, such as 10 to 15 mJ/pulse, and still ablate the blocking tissues. At these low power levels, the Er:YAG laser does not melt the nylon suture 174 when the laser is being fired at the blocking tissue 176.

Figure 10:
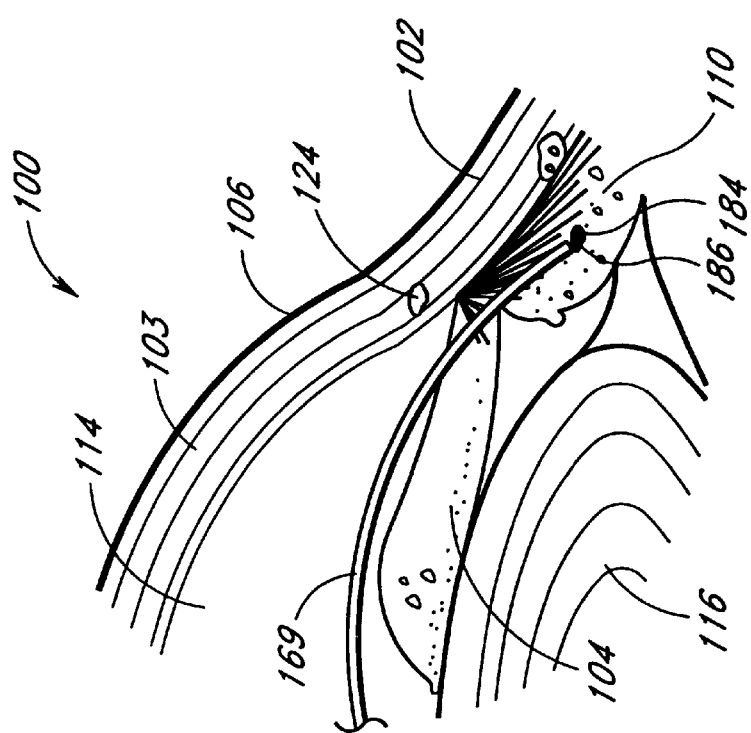
FIG. 10 is an enlarged view of the portion of a human eye indicated in FIG. 9 which is undergoing the procedure to reopen the openings in the ciliary body.

In accordance with another procedure as illustrated in FIGS. 9–10, an Er:YAG laser 138 (FIG. 3) is used to reopen the blocked passages in the ciliary body, or more particularly, in the ciliary process of the ciliary body 110. The laser 138 is coupled to a laser probe 167 comprising a flexible optical fiber 169, as described in association with the Schlemm's canal procedure above. A first passageway 178 is formed in a side 180 of the eye 100 opposite from the ciliary body that is to be reopened. The surgeon forms a self-sealing V-shaped incision 182 in the conjunctival tissue 106 at the side 180 to permit entry of the probe 167. The fiber 169 is inserted into the incision site 182 and is positioned proximal to the targeted conjunctival tissue 106. The fiber 169 is advanced through the conjunctival tissue 106 as the laser 138 (FIG. 3) is activated. Once the fiber 169 has passed through the conjunctival tissue 106, the fiber 169 is continuously advanced while the laser 138 is activated until the first passageway 178 extends completely through the sclera 102 and opens into the anterior chamber 104 of the eye 100. As will be recognized by those of skill in the art this first passageway 178 may be formed by mechanical means rather than by the laser probe 167 and laser 138. For example, a scalpel may be used to cut through the conjunctiva 106 and sclera 102.

After being advanced through the anterior chamber 114, the end 171 of the fiber 169 is positioned proximate one of the occluded apertures 184 of the ciliary body 110. The laser 138 is activated for several pulses until the blocking tissue 186 is ablated. If necessary, the fiber 169 is further advanced to reach deeper blocking tissue 186 and the laser 138 is activated for several pulses to ablate the deeper blocking tissue 186, until the natural opening 184 of the ciliary body 110 is reopened. The end 171 of the fiber 169 can be repositioned proximate another opening 184 in the ciliary body 110 that is obstructed. The laser 138 is again activated for several pulses until the blocking tissue 186 is ablated. The process of repositioning the fiber end 171 proximate an obstructed opening 184 and firing the laser 138 is repeated until the blocking tissue 186 is removed from the desired number of blocked openings 184 in the ciliary body 110. With the blocking tissue 186 removed from openings 184 in the ciliary body 110, the aqueous humor 118 from the anterior chamber 114 can once again flow from the anterior chamber 114 through the ciliary body 110 to maintain the desired pressure within the eye 100, thus relieving the glaucoma condition.

In another procedure, the same process described above for removing blocking tissue 186 from the ciliary body 110 can be used to remove blocking tissue 186 from the trabecular meshwork 121. In this case, the laser probe 167 is advanced through the anterior chamber 114 and is positioned proximate one of the occluded apertures 188 of the trabecular meshwork 121. The laser 138 is activated for several pulses until the blocking tissue 186 is ablated. If necessary, the fiber 169 is further advanced to reach deeper blocking tissue 186 and the laser 138 is activated for several pulses to ablate the deeper blocking tissue 186, until the opening 188 of the trabecular meshwork 121 is unobstructed. The end of the fiber 169 can be repositioned proximate another opening 188 in the trabecular meshwork 121 that is obstructed. The laser 138 is again activated for several pulses until the blocking tissue 186 is ablated. The process of repositioning the fiber end 171 proximate an obstructed opening 188 and firing the laser 138 is repeated until the blocking tissue 186 is removed from the blocked openings 188 in the trabecular meshwork 121. When the blocking tissue 186 is removed from openings 188 in the trabecular meshwork 121, the aqueous humor 118 from the anterior chamber 114 can once again flow from the anterior chamber 114 through the trabecular meshwork 121 to maintain the desired pressure within the eye 100, thus relieving the glaucoma condition.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed is:

1. A method of removing a blockage in Schlemm's canal using a laser and a laser probe, said method comprising:

advancing a suture into Schlemm's canal until the suture comes into contact with tissue blocking the canal;

following the path of the suture with said laser probe until the laser probe is proximal to said tissue blocking the canal; and activating a laser to apply pulsed laser energy to the tissue blocking the canal thereby ablating the occluding tissue to reopen Schlemm's canal.

2. The method of claim 1, wherein said laser is an Er:YAG laser which is pulsed at a pulse rate of about 5 to 10 Hz, a pulse duration of about 250 $\mu$s to 300 $\mu$s, and produces energy of about 10 to 15 mJ per pulse.

3. The method of claim 1, wherein said suture extends further into the canal than the laser probe when the laser is activated to apply laser energy to the tissue.

* * * * *